US006878751B1

(12) United States Patent
Donnelly et al.

(10) Patent No.: US 6,878,751 B1
(45) Date of Patent: Apr. 12, 2005

(54) ADMINISTRATION OF RESVERATROL TO TREAT INFLAMMATORY RESPIRATORY DISORDERS

(75) Inventors: Louise Elizabeth Donnelly, London (GB); Peter John Barnes, London (GB)

(73) Assignees: Imperial College of Science Technology and Medicine, London (GB); Imperial College Innovations Limited, London (GB)

( * ) Notice: Subject to any disclaimer, the term of this patent is extended or adjusted under 35 U.S.C. 154(b) by 182 days.

(21) Appl. No.: 09/694,108

(22) Filed: Oct. 19, 2000

(51) Int. Cl.[7] ............................................... A61K 31/05
(52) U.S. Cl. ........................ 514/733; 514/734; 514/736
(58) Field of Search ................................ 514/733, 734, 514/736

(56) References Cited

U.S. PATENT DOCUMENTS

| | | | | |
|---|---|---|---|---|
| 4,176,180 A | * | 11/1979 | Barbier ........................ | 514/29 |
| 5,411,986 A | | 5/1995 | Cho et al. | |
| 5,747,536 A | | 5/1998 | Cavazza | |
| 6,022,901 A | | 2/2000 | Goodman | |
| 6,329,422 B1 | | 12/2001 | Fischer et al. ............... | 514/456 |
| 6,414,037 B1 | | 7/2002 | Pezzuto et al. ............. | 514/733 |
| 6,551,616 B1 | * | 4/2003 | Notario et al. ............... | 424/464 |

FOREIGN PATENT DOCUMENTS

| | | |
|---|---|---|
| EP | 1138323 A2 | 10/2001 |
| WO | 9404148 * | 3/1994 |
| WO | WO 00/13685 | 3/2000 |
| WO | WO 00/38620 | 7/2000 |
| WO | WO 01/08671 | 2/2001 |

OTHER PUBLICATIONS

Goodman & Gilman's, The Pharmacological Basis of Therapeutics, Ninth Edition, Chapter 28, pp. 666–669 (1996).*
American Drug Index, 42nd Edition, pp. 674, 746 (1998).*
Ashby et al. (1999), "Partial and Weak Oestrogenicity of the Red Win Constituent Resveratrol: Consideration of its Superagonist Activity in MCF–7 Cells and its Suggested Cardiovascular Protective Effects," *J. Appl. Toxicol.* 19:39–45.
Barner et al. (1998), "Transcription Factors and Asthma," *Eur. Respir. J.* 12(1):221–234.
Bertelli et al. (1995) "Antiplatelet Activity of Synthetic and Natural Resveratrol in Red Wine," *Inst. J. Tiss. Reac.* XVII(1):1–3.
Bertram (1979), "Reduction in the Formation of Cardinogen–Induced Transformed Foci by Penicillin G Sodium in the C3H/10T$_{1/2}$ CL8 Cell Line," *Cancer Lett.* 7:289–298.
Blackwell et al. (1997), "The Role of Nuclear Factor–κB in Cytokine Gene Regulation," *Am. J. Respir. Cell Mol. Biol.* 17:3–9.

Bowers et al. (2000), "Resveratrol Acts as a Mixed Agonist/Antagonist for Estrogen Receptors Alpha and Beta," *Endocrinology* 141(10):3657–3667.
Cazzola et al. (2000), "Potential Role of Macrolides in the Treatment of Asthma," *Monaldi Arch. Chest Dis.* 55(3):231–236.
Damianaki et al. (2000), "Potent Inhibitory Action of Red Wine Polyphenols on Human Breast Cancer Cells," *Journal of Cellular Biochemistry* 78:429–441.
Dweik et al. (1997), "Nitric Oxide Synthase in the Human Airway Epithelium," *Acta Pharmacologica Sinica* 18(6):550–552.
ElAttar et al. (1999), "Modulating Effect of Resveratrol and Quercetin on Oral Cancer Cell Growth and Proliferation," *Anti–Cancer Drugs* 10:187–193.
Frankel et al. (1993) "Inhibition of Human LDL Oxidation by Resveratrol," *The Lancet* 341:1103–1104.
Fröde–Saleh et al. (2000), "Synergistic Antiinflammatory Effect of NF–78 B Inhibitors and Steroidal or Non Steroidal Antiinflammatory Drugs in the Pleural Inflammation Induced by Carrageenan in Mice," *Inflammation Research* 49(7):330–337.
Gerhäuser et al. (1995), "Retinoids Mediate Potent Cancer Chemopreventive Activity Through Transcriptional Regulation of Ornithine Decarboxylase," *Nature Med.* 1(3)260–266.
Goldberg et al. (1994) "Direct Injection Gas Chromatographic Mass Spectrometric Assay for trans–Resveratrol," *Anal. Chem.* 66:3959–3963.
Goldberg et al. (1995), "Direct Gas Chromatographic— Mass Spectrometric Method to Assay cis–Resveratrol in Wines: Preliminary Survey of Its Concentration in Commercial Wines," *J. Agric. Food Chem.* 43:1245–1250.
Goldberg et al. (1995) "A Global Survey of Trans–Resveratrol Concentrations in Commercial Wines," *Am. J. Enol. Vitic.* 46(2):159–165.
Goldberg et al. (1996) "Method to Assay the Concentrations of Phenolic Constituents of Biological Interest in Wines," *Anal. Chem.* 68:1688–1694.
Goodwin (1984), "Immunologic Effects of Nonsteroidal Anti–Inflammatory Drugs," *Am. J. Med.* 77:7–15.

(Continued)

*Primary Examiner*—Raymond Henley, III
*Assistant Examiner*—Cybille Delacroix-Muirheid
(74) *Attorney, Agent, or Firm*—Karen Canaan; Reed Intellectual Property Law Group

(57) ABSTRACT

A method is provided for treating inflammatory respiratory disorders such as asthma and chronic obstructive pulmonary disease (COPD). The method involves administration, preferably oral or pulmonary administration, of an active agent selected from the group consisting of resveratrol, pharmacologically acceptable salts, esters, amides, prodrugs and analogs thereof, and combinations of any of the foregoing. Pharmaceutical formulations for use in conjunction with the aforementioned method are provided as well.

20 Claims, No Drawings

OTHER PUBLICATIONS

Guo et al. (1997), "Interferon γ and Interleukin 4 Stimulate Prolonged Expression of Inducible Nitric Oxide Synthase in Human Airway Epithelium Through Synthesis of Soluble Mediators," *J. Clin. Invest.* 100(4):829–838.

Guo et al. (1998), "Characterization of Inducible Nitric Oxide Synthase Expression in Human Airway Epithelium," *Environ. Health Perspect.* 106(Suppl. 5):1119–1124.

Guo et al. (2000), "Molecular Mechanisms of Increased Nitric Oxide (NO) in Astham: Evidence for Transcriptional and Post–Translational Regulation of NO Synthesis," *J. Immunol.* 164(11):5970–5980.

Jang et al. (1997) "Cancer Chemopreventive Activity of Resveratrol, a Natural Product Derived from Grapes," *Science* 275:218–220.

Jayatilake et al. (1993), "Kinase Inhibitors From Polygonum Cuspidatum," *J. Nat. Proc.* 56(10):1805–1810.

Jeandet et al. (1991) "The Production of Reseveratrol 3,5, 4'–Trihydroxystilbene) by Grape Berries in Different Developmental Stages," *Am. J. Enol. Vitic.* 42(1):41–46.

Kawanda et al. (1998), "Effect of Antioxidants, Resveratrol, Quercetin, and N–Acetylcysteine, on the Functions of Cultured Rat Hepatic Stellate Cells and Kupffer Cells," *Hepatology* 27(5):1265–1274.

Kulmacz et al. (1987), "Cycl–Oxygenase: Measurement, Purification and Properties," *Prostaglandins and Related Substances*, IRL Press, Oxford, pp. 209–277.

Landolph (1985), "Chemical Transformation in C3H $10T_{1/2}$ C18 Mouse Embryo Fibroblasts: Hstorical Background, Assessment of the Transformation Assay, and Evolution and Optimization of the Transformation Assay Protocol," *Transformation Assay of Established Cell Lines: Mechanisms and Application,* T. Kakunaga et al., eds., Oxford Univ. Press, Toronto, pp. 185–199.

Lee et al. (1994), "Protection of Cell Injury Against Oxidative Stress By Resveratrol," *Society for Neuroscience Abstracts* 20(2):1648.

Manna et al. (2000), "Resveratrol Suppresses TNF–Induced Activation of Nuclear Transcription Factors NF–κB, Activator Protein–1, and Apoptosis: Potential Role of Reactive Oxygen Intermediates and Lipid Peroxidation," *J. Immunol.* 164(12):6509–6519.

Mannila et al. (1993), "Anti–Leukaemic Compounds Derived From Stilbenes in *Picea Abies* Bark," *Phytochemistry* 33(4):813–816.

Martinez et al. (2000), "Effect of Resveratrol, a Natural Polyphenolic Compound, on Reactive Oxygen Species and Prostaglandin Production," *Biochem. Pharmacol.* 59:865–870.

Misko et al. (1993), "A Fluorometric Assay for the Measurement of Nitrite in Biological Samples," *Anal. Biochem.* 214:11–16.

Mondal et al. (1976), "Two–Stage Chemical Oncogenesis In Cultures of C3H/10T1/2Cells," *Cancer Res.* 36:2254–2260.

Moon et al. (1990), "Retinoid Inhibition of Experimental Carcinogenesis," *Chemistry and Biology of Synthetic Retinoids,* M.I. Dawson et al., eds., CRC Press, Boca Raton, FL, 501–518.

Moren–Mañas. (1985) "Dehydroacetic Acid Chemistry, A New Synthesis of Resveratrol, a Phytoalexine of *Vitis Vinifera,*" *Anal. Quim* 81:157–161.

Newton et al. (1996), "Superinduction of NF–κB by Actinomycin D and Cycloheximide in Epithelial Cells," *Bichem. Biophys. Res. Commun.* 218:518–523.

Pace–Asciak et al. (1995), "The Red Wine Phenolics Trans–Resveratrol and Quercetin Block Human Platelet Aggregation and Eicosanoid Synthesis: Implications for Protection Against Coronary Heart Disease," *Clinica Chimica Acta* 235:207–219.

Pang et al. (2000), "Synergistic Inhibition by $\beta_2$–Agonists and Corticosteroids on Tumor Necrosis Factor–α–Induced Interleukin–8 Release from Cultured Human Airway Smooth–Muscle Cells," *Am. J. Respir. Cell Mol. Biol.* 23(1):79–85.

Plescia et al. (1975), "Subversion of Immune System By Tumor Cells and Role of Prostaglandins," *Proc. Natl. Acad. Sci., USA* 72(5):1848–1851.

Prochaska et al. (1988), "Direct Measurement of NAD-(P)H:Quinone Reductase From Cells Cultured in Microtiter Wells; A Screening Assay for Aniticarcinogenic Enzyme Inducers," *Anal. Biochem.* 169:328–336.

Reznikoff et al. (1973), "Quantitative and Qualitative Studies of Chemical Transformation of Cloned C3H Mouse Embryo Cells Sensitive to Postconfluence Inhibition of Cell Division," *Cancer Res.* 33:3239–3249.

Sharmon et al. (1994), "A Correlative Approach For the Identification of Antimutagens That Demonstrate Chemopreventive Activity," *Anticancer Res.* 14:1775–1778.

Sharma et al. (1994), "Screening of Potential Chemopreventive Agents Using Biochemical Markers of Carcinogenesis," *Cancer Res.* 54:5848–5855.

Slowing et al. (1994), "Anti–Inflammatory Activity of Leaf Extracts of Eugenia Jambos in Rats," *J. of Ethnopharmacol.* 43:9–11.

Soleas et al. (1995), "A Derivatized Gas Chromatographic–Mass Spectrometric Method for the Analysis of Both Isomers of Resveratrol in Juice and Wine," *Am. J. Enol. Vitic.* 46(3):346–352.

Sporn et al. (1979), "Chemoprevention of Cancer With Retinoids," *Federation Proceedings* 38(11):2528–2534.

Subbaramaiah et al. (1998), "Resveratrol Inhibits Cyclooxygenase–2 Transcription and Activity in Phorbol Ester–Treated Human Mammary Epithelial Cells," *J. Biol. Chem.* 273(34):21875–21882.

Suh et al. (1995) "Discovery of Natural Product Chemopreventive Agents Utilizing HL–60 Cell Differentiation as a Model," *Anticancer Res.* 15:233–240.

Tardif et al. (1997) "Probucol and Multivitamins in the Prevention of Restenosis After Coronary Angioplasty," *The New Eng. J. Medicine* 337(6):365–372.

van der Ouderaa et al. (1982), "Purification of PGH Synthase From Sheep Vesicular Glands," *Methods Enzymol.* 86:60–68.

Wadsworth et al. (1999), "Effects of the Wine Polyphenolics Quercetin and Resveratrol on Pro–Inflammatory Cytokine Expression in RAW 264.7 Macrophages," *Biochem. Pharmacol.* 57:941–949.

Wattenberg (1993), "Prevention–Therapy–Basic Science and the Resolution of the Cancer Problem: Presidential Address," *Cancer Research* 53:5890–5896.

Wild et al. (1987), "Prostaglandin H Synthase–Dependent Mutagenic Activation of Heterocyclic Aromatic Amines of the IQ–Type," *Carcinogenesis* 8(4):541–545.

Zenser et al. (1983), "Prostaglandin H Synthase–Catalyzed Activation of Benzidine: A Model To Assess Pharmacologic Intervention of the Initiation of Chemical Carcinogenesis," *J. Pharmacol. Exp. Ther.* 227(3):545–550.

Zhang et al. (1994), "Anticarcinogenic Activities of Sulforaphane and Structuraly Related Synthetic Norbornyl Isothiocyanates," *Proc. Natl. Acad. Sci., USA* 91:3147–3150.

Miura et al. (1997), "Dietary Considerations for Cancer Prevention," *Igaku no Ayumi* (*Biochemistry of the Dining Table: Series 9*) 183(8):530–536 (English translation of abstract only).

Sanders et al. (1997), Occurrence of Resveratrol in Edible Peanuts, *Abstracts of Papers* (*Part 2*), 214th ACS National Meeting 8412–3530–9, American Chemical Society, Sep. 7–11, 1997, AFGD:033.

Sharkey et al. (1999), "Initial Serum Ferritin Levels in Patients with Multiple Trauma and the Subsequent Development of Acute Respiratory Distress Syndrome," *Am. J. Respir. Crit. Care Med.* 159:1506–1509.

Bertelli et al. (1998), "Modulatory Effect of Resveratrol, a Natural Phytoalexin, on Endothelial Adhesion Molecules and Intracellular Signal Transduction," *Pharmaceutical Biology* 36(Supp.):44–52.

Koh et al. (2001), "Resveratrol Derivatives Showing the Leukotriene D4 Antogonism," *Agric. Chem. Biotechnol.* 44(1):32–34.

Tsuruga et al. (1991), "Biologically Active Constituents of Melaleuca Leucadendron: Inhibitors of Induced Histamine Released from Rat Mast Cells," *Chemical and Pharmaceutical Bulletin* 39(12):3276–3278, Pharmaceutical Society of Japan.

Anderson et al., Remington's Pharmaceutical Sciences, 15th Edition, Mack Publishing Co. (1975), pp. 1554, 1571, 1575.*

* cited by examiner

ADMINISTRATION OF RESVERATROL TO TREAT INFLAMMATORY RESPIRATORY DISORDERS

TECHNICAL FIELD

The present invention relates generally to methods and compositions for the treatment of inflammatory respiratory disorders including bronchitis and asthma. More particularly, the invention relates to administration of resveratrol (3,5,4'-trihydroxystilbene) and analogs thereof that are useful, for example, in the treatment of asthma, chronic obstructive pulmonary disease (COPD), including chronic bronchitis, and other chronic inflammatory lung diseases including cystic fibrosis, bronchiectasis and interstitial lung diseases (ILD). The invention finds utility in the fields of medicine, pharmacology and drug delivery.

BACKGROUND

It has been noted that there are a number of biologically active phenolic compounds present in wine, particularly red wine. Such compounds include, for example, catechin, epicatechin, quercetin, rutin, trans-resveratrol, cis-resveratrol, cis-resveratrol glucoside and trans-resveratrol glucoside. See, e.g., Goldberg et al. (1996) *Anal Chem.* 68:1688–1694. These compounds have been shown to protect low-density lipoproteins against oxidation. The resveratrol isomers, in particular, have been found to promote vascular relaxation through the generation of nitric oxide by the endothelium, and to modulate eicosanoid synthesis in a manner that suggests use in preventing coronary artery occlusion and consequently acute and chronic ischemic heart disease, including myocardial infarction. Id. at pp. 1688–89). This discovery appears to explain the studies demonstrating that moderate consumption of red wine tends to have a protective effect against heart disease. Bertelli et al. (1995) *Inst. J. Tiss. Reac.* XVII(1):1–3.

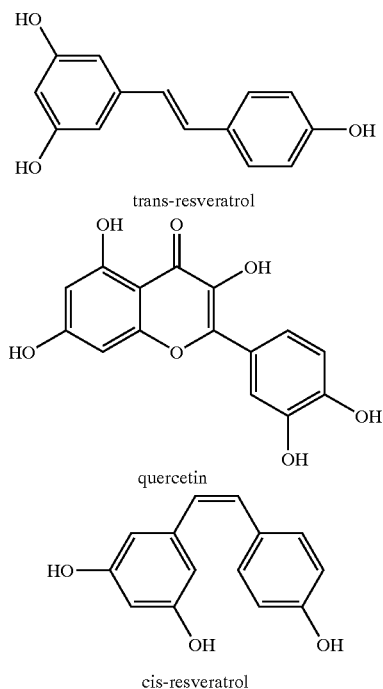

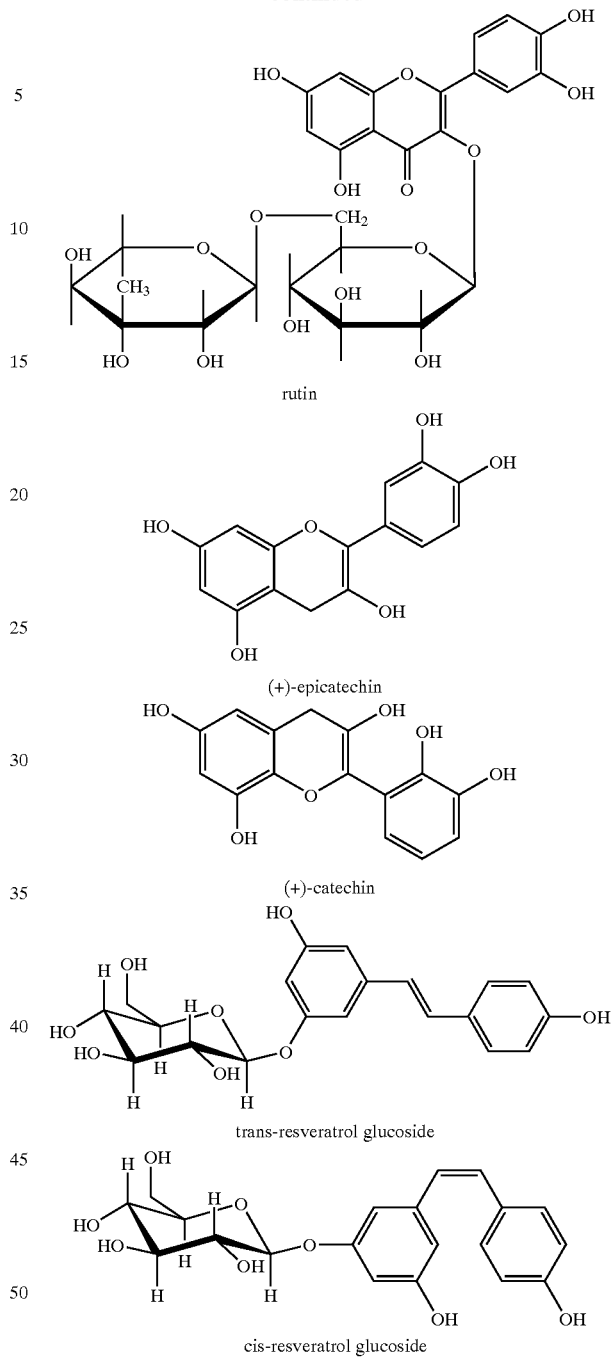

Resveratrol (3,5,4'-trihydroxystilbene) has been identified as a constituent not only of grape skins (Soleas et al. (1995) *Am. J. Enol. Vitic.* 46(3):346–352) but has also been found to be present in ground nuts, eucalyptus, and other plant species. Goldberg et al. (1995), *Am. J. Enol. Vitic.* 46(2): 159–165. A great deal of interest has been focused on the compound's antifungal activity and its correlation with resistance to fungal infection. Id at 159. Resveratrol may be obtained commercially (typically as the trans isomer, e.g. from the Sigma Chemical Company, St. Louis, Mo.), or it may be isolated from wine or grape skins, or it may be chemically synthesized. Synthesis is typically carried out by a Wittig reaction linking two substituted phenols through a styrene double bond, as described by Moreno-Manas et al.

(1985) Anal. Quim 81:157–61 and subsequently modified by others (Jeandet et al. (1991) Am. J. Enol. Vitic. 42:41–46; Goldberg et al. (1994) Anal. Chem. 66: 3959–63).

There are more studies concerning trans-resveratrol than the cis isomer; however, the cis isomer appears to be equally important from a biological standpoint. Numerous uses have been proposed and evaluated for the resveratrol isomers. Jang et al. (1997) Science 275:218–220, show that resveratrol has cancer chemopreventive activity in assays representing three major stages of carcinogenesis. That is, the authors found that the compound: (1) acted as an antioxidant and antimutagen and induced phase II drug-metabolizing enzymes; (2) mediated anti-inflammatory effects and inhibited cyclooxygenase and hydroperoxidase; and (3) induced human promyelocytic leukemia cell differentiation. In addition, as noted above, resveratrol has been extensively studied for its correlation to the cardiovascular utility of red wine. See, e.g., Bertelli et al., supra; Pace-Asciak et al. (1995), Clinica Chimica Acta 235:207–2191; and Frankel et al. (Apr. 24, 1993), The Lancet 341:1104. Neurologic uses have also been proposed (Lee et al. (1994), Society for Neuroscience Abstracts 20(1–2): 1648). More recently resveratrol has been shown to inhibit COX-2 transcription (Subbaramaiah et al. (1998) J. Biol. Chem. 273:21875–82; Martinez et al. (2000) Biochem. Pharmacol. 59:865–70), as well as inhibiting COX-1 enzymatic activity (Jang et al. (1997) Science 275:218–20), suggesting that resveratrol exerts an effect on transcription by affecting transcription factors, in addition to NSAID-like direct inhibition of COX enzymatic activity. Recent evidence suggests that macrolide antibiotics have a steroid-sparing antiinflammatory effect that is independent of their antibiotic activity and any effect on steroid metabolism (Cazzola et al. (2000) Monaldi Arch. Chest Dis. 55(3):231–6). The mechanism of macrolide reduction of bronchial hyperresponsiveness in asthmatics suggested by the evidence resembles the mechanism suggested by Jang et al. (2000), supra, a combination of inhibition of COX and increased synthesis of antiinflammatory cytokines, inhibiting initial chemotaxis of PMNs and the mixed lymphocyte response which ultimately results in eosinophilic inflammation seen in bronchial inflammation (Cazzola et al.(2000), supra).

In addition, resveratrol has found to be useful as a cancer chemopreventive agent. Known cancer chemopreventive agents include nonsteroidal antiinflammatory drugs (NSAIDs) such as indomethacin, aspirin, piroxicam, and sulindac, all of which inhibit cyclooxygenase, abbreviated hereafter as COX. A COX inhibitory activity is important in cancer chemoprevention because COX catalyzes the conversion of arachidonic acid to proinflammatory substances, such as prostaglandins, which can stimulate tumor cell growth and suppress immune surveillance. Plescia et al. (1975) Proc. Natl. Acad. Sci. USA. 72:1848; Goodwin (1984) Am. J. Med. 77:7. In addition, COX can activate carcinogens to forms that damage genetic material. Zenser et al. (1983) J. Pharmacol. Exp. Ther. 227:545; Wild et al. (1987) Carcinogenesis 8:541. Investigators have searched for new cancer chemopreventive agents by evaluating hundreds of plant extracts for a potential to inhibit COX. An extract derived from Cassia quinquangulata Rich. (Leguminosae) was identified as a potent COX inhibitor, and on the basis of bioassay-guided fractionation, trans-resveratrol was identified as the active compound. See Mannila et al. (19983) Phytochemistry 33:813, and Jayatilake et al. (1993) J. Nat. Prod. 5:1805.

To date, however, administration of resveratrol to treat inflammatory respiratory disorders is unknown. The present invention is premised on the unexpected finding that administration of resveratrol is extremely effective in treating inflammatory respiratory disorders, and is even more effective than oral, parenteral or pulmonary administration of corticosteroids.

SUMMARY OF THE INVENTION

Accordingly, it is a primary object of the invention to address the above-mentioned need in the art by providing a method for treating inflammatory respiratory diseases, including asthma and COPD.

It is another object of the invention to provide such a method by administering to a patient a formulation comprising an active agent selected from the group consisting of resveratrol, pharmacologically acceptable salts, esters, amides, prodrugs and analogs thereof, and combinations of any of the foregoing.

It is another object of the invention to provide such a method wherein the formulation is administered orally.

It is still another object of the invention to provide such a method wherein the formulation is administered to the lungs.

It is a further object of the invention to provide such a method by administering resveratrol in stereoisomerically pure form, i.e., in either the cis or the trans form.

It is still a further object of the invention to provide novel pharmaceutical formulations for pulmonary administration, comprising an active agent selected from the group consisting of resveratrol, pharmacologically acceptable salts, esters, amides, prodrugs and analogs thereof, and combinations of any of the foregoing, in combination with a pharmaceutically acceptable carrier suitable for pulmonary drug delivery.

Additional objects, advantages and novel features of the invention will be set forth in part in the description which follows, and in part will become apparent to those skilled in the art upon examination of the following, or may be learned by practice of the invention.

In one embodiment, then, a method is provided for preventing or treating a patient suffering or prone to an inflammatory respiratory condition, the method comprising administering to the individual a pharmaceutical composition comprising a therapeutically effective amount of an active agent selected from the group consisting of resveratrol, pharmacologically acceptable salts, esters, amides, prodrugs and analogs thereof, and combinations of any of the foregoing. Generally, the active agent will be cis-resveratrol, trans-resveratrol, or a complex in which one or more of the compounds' hydroxyl groups are conjugated to a mono- or di-saccharide, e.g., cis-resveratrol glucoside, trans-resveratrol glucoside, etc. However, as will be appreciated by those skilled in the art, and as discussed in detail elsewhere herein, other forms of the active agents may also be used. The respiratory disorder may be, for example, atopic and non-atopic asthma and COPD (which includes chronic bronchitis, emphysema) and diffuse interstitial pulmonary fibrosis (DIPF), also known as interstitial lung disorder (ILD).

In another embodiment, a pharmaceutical formulation is provided for pulmonary administration, comprising an active agent as described above, with cis-resveratrol, trans-resveratrol, and conjugates of cis-resveratrol or trans-resveratrol with mono- or di-saccharides preferred. The formulation also comprises a pharmaceutically acceptable carrier suitable for pulmonary drug administration. The formulation may contain one or more additional active agents and/or excipients, provided the excipients do not have a deleterious effect on a patient or a deleterious chemical or physical effect on any component in the formulation.

DETAILED DESCRIPTION OF THE INVENTION

Before the present invention is described in detail, it is to be understood that unless otherwise indicated this invention is not limited to any particular formulation, carrier, or drug administration regimen, as such may vary. It is also to be understood that the terminology used herein is for the purpose of describing particular embodiments only and is not intended to limit the scope of the present invention.

It must be noted that as used herein and in the claims, the singular forms "a," "and" and "the" include plural referents unless the context clearly dictates otherwise. Thus, for example, reference to "an active agent" in a formulation includes two or more active agents, reference to "a carrier" includes two or more carriers, and so forth.

In this specification and in the claims which follow, reference will be made to a number of terms which shall be defined to have the following meanings:

The terms "active agent," "drug" and "pharmacologically active agent" are used interchangeably herein to refer to a chemical material or compound which, when administered to an organism (human or animal) induces a desired pharmacologic effect. Included are derivatives and analogs of those compounds or classes of compounds specifically mentioned that also induce the desired pharmacologic effect.

By "pharmaceutically acceptable carrier" is meant a material or materials that are suitable for drug administration and not biologically or otherwise undesirable, i.e., that may be administered to an individual along with an active agent without causing any undesirable biological effects or interacting in a deleterious manner with any of the other components of the pharmaceutical formulation in which it is contained.

Similarly, a "pharmacologically acceptable" salt, ester or other derivative of an active agent as provided herein is a salt, ester or other derivative that is not biologically or otherwise undesirable.

By the terms "effective amount" or "therapeutically effective amount" of an agent as provided herein are meant a nontoxic but sufficient amount of the agent to provide the desired therapeutic effect. The exact amount required will vary from subject to subject, depending on the age, weight, and general condition of the subject, the severity of the condition being treated, the judgment of the clinician, and the like. Thus, it is not possible to specify an exact "effective amount." However, an appropriate "effective" amount in any individual case may be determined by one of ordinary skill in the art using only routine experimentation.

The terms "treating" and "treatment" as used herein refer to reduction in severity and/or frequency of symptoms, elimination of symptoms and/or underlying cause, prevention of the occurrence of symptoms and/or their underlying cause, and improvement or remediation of damage. Thus, for example, the present method of "treating" asthma, as the term "treating" is used herein, encompasses both prevention of asthma in a predisposed individual and treatment of asthma in a clinically symptomatic individual.

The terms "condition," "disease" and "disorder" are used interchangeably herein as referring to a physiological state that can be prevented or treated by administration of a pharmaceutical formulation as described herein.

The term "patient" as in treatment of "a patient" refers to a mammalian individual afflicted with or prone to a condition, disease or disorder as specified herein, and includes both humans and animals.

The term "pulmonary" as used herein refers to any part, tissue or organ that is directly or indirectly involved with gas exchange, i.e., $O_2/CO_2$ exchange, within a patient. "Pulmonary" contemplates both the upper and lower airway passages and includes, for example, the mouth, nose, pharynx, oropharynx, laryngopharynx, larynx, trachea, carina, bronchi, bronchioles and alveoli. Thus, the phrase "pulmonary drug administration" refers to administering the formulation described herein to any part, tissue or organ that is directly or indirectly involved with gas exchange within a patient.

The term "resveratrol" is intended to mean either the cis-isomer of resveratrol, the trans-isomer of resveratrol, or a mixture of the two isomers. The term is also intended to include both the naturally occurring active agent and the compound as it may be chemically synthesized in the laboratory. Further, when the term "resveratrol" is used herein, it is intended to encompass pharmacologically acceptable salts, esters, amides, prodrugs and analogs of resveratrol.

"Optional" or "optionally" means that the subsequently described circumstance may or may not occur, so that the description includes instances where the circumstance occurs and instances where it does not. For example, recitation of an additive as "optionally present" in a formulation herein encompasses both the formulation containing the additive and the formulation not containing the additive.

The invention, as noted above, involves the administration of resveratrol to an individual in order to treat an inflammatory respiratory disorder. The resveratrol may be administered in natural form, i.e., as isolated from grape skins, wine or other plant-derived compositions, or it may be administered as chemically synthesized in the laboratory (e.g., using the methods of Moreno-Manas et al., Jeandet et al., or Goldberg et al. (1994), cited earlier herein), or as obtained commercially, e.g., from the Sigma Chemical Company (St. Louis, Mo.). Preferred methods for obtaining resveratrol from a natural source is to extract the compound from *P. capsudatum* or from the dried roots of *C. quinquangulata* which may be harvested in Peru. The dried ground plant material may be extracted with a suitable solvent, e.g., methanol, preferably followed by concentration and dilution with water. After washing with hexane or an equally suitable nonpolar organic solvent, the aqueous layer may be partitioned with, for example, ethyl acetate. The ethyl acetate extract is then separated into fractions using, for example, chloroform-methanol (0 to 30% methanol) as eluent over a silica gel chromatographic column. Fractions with higher concentrations of resveratrol may be combined and subjected to further column chromatography until the product is obtained in sufficiently high yield.

The active agent may be administered in the form of a pharmacologically acceptable salt, ester, amide, prodrug or analog or as a combination thereof. Salts, esters, amides, prodrugs and analogs of resveratrol may be prepared using standard procedures known to those skilled in the art of synthetic organic chemistry and pharmaceutical formulation, described, for example, by J. March, "*Advanced Organic Chemistry: Reactions, Mechanisms and Structure,*" 4th Ed. (New York: Wiley-Interscience, 1992), and in *Remington's Pharmaceutical Sciences, 19th* Ed. (Easton, Pa.: Mack Publishing Company, 1995). For example, basic addition salts are prepared from the neutral drug using conventional means, involving reaction of one or more of the active agent's free hydroxyl groups with a suitable base. Generally, the neutral form of the drug is dissolved in a polar organic solvent such as methanol or ethanol and the base is added thereto. The resulting salt either precipitates or may be brought out of solution by addition of a less polar solvent. Suitable bases for forming basic addition salts include, but are not limited to, inorganic bases such as sodium hydroxide, potassium hydroxide, ammonium hydroxide, calcium hydroxide, trimethylamine, or the like. Preparation of esters involves functionalization of hydroxyl groups which may be present within the molecular structure of the drug. The esters are typically acyl-substituted derivatives of free alcohol groups, i.e., moieties which are derived from carboxylic acids of the formula RCOOH where R is alkyl, and preferably is lower alkyl. Esters can be reconverted to the free acids, if desired, by using conventional hydrogenolysis or hydrolysis procedures. Preparation of amides and prodrugs can be carried out in an analogous manner. Other derivatives and analogs of the active agents may be prepared using standard techniques known to those skilled in the art of synthetic organic chemistry, or may be deduced by reference to the pertinent literature.

Preferred derivatives of cis- and trans-resveratrol are those in which one or more of the compounds' hydroxyl groups, typically the 3-hydroxyl group, is conjugated to a mono- or di-saccharide, generally the 1-position of a monosaccharide. Examples of saccharides which may be conjugated to the resveratrol molecule include, but are not limited to, glucose, galactose, maltose, lactose and sucrose. Cis-resveratrol glucoside and trans-resveratrol glucoside are particularly preferred.

Accordingly, the invention encompasses pharmaceutical formulations comprising resveratrol or an analog thereof in association with a pharmaceutical carrier or diluent. The formulation can be administered orally, by parenteral (intramuscular, intraperitoneal, intravenous or subcutaneous) injection, or using pulmonary delivery. The formulations are provided in dosage forms appropriate for each route of administration.

Solid dosage forms for oral administration include capsules, tablets, pills, powders, and granules. In solid dosage forms, the active agent is admixed with at least one inert pharmaceutically acceptable carrier such as sucrose, lactose, or starch. Such dosage forms can also comprise, as is normal practice, an additional substance other than an inert diluent, e.g., a lubricating agent such as magnesium stearate. With capsules, tablets, and pills, the dosage forms may also comprise a buffering agent. Tablets and pills can additionally be prepared with enteric coatings.

Liquid dosage forms for oral administration include pharmaceutically acceptable emulsions, solutions, suspensions and syrups, with the elixirs containing an inert diluent commonly used in the art, such as water. These compositions can also include one or more adjuvants, such as a wetting agent, an emulsifying agent, a suspending agent, a sweetening agent, a flavoring agent or a perfuming agent.

Preparations for parenteral administration include sterile aqueous or non-aqueous solutions, suspensions, and emulsions. Examples of non-aqueous solvents or vehicles are propylene glycol, polyethylene glycol, vegetable oils, such as olive oil and corn oil, gelatin, and injectable organic esters such as ethyl oleate. Such dosage forms may also contain one or more adjuvants such as a preserving agent, a wetting agent, an emulsifying agent and a dispersing agent. The dosage forms may be sterilized by, for example, filtration through a bacteria-retaining filter, by incorporating sterilizing agents into the compositions, by irradiating the compositions, or by heating the compositions. They can also be manufactured using sterile water, or some other sterile injectable medium, prior to use.

Pharmaceutical formulations for oral or parenteral administration may also comprise a resveratrol-containing microemulsion, and may contain alternative pharmaceutically acceptable carriers, vehicles, additives, etc. particularly suited to oral or parenteral drug administration. Alternatively, a resveratrol-containing microemulsion may be administered orally or parenterally without modification.

Microemulsions are thermodynamically stable, isotropically clear dispersions of two immiscible liquids, such as oil and water, stabilized by an interfacial film of surfactant molecules (*Encyclopedia of Pharmaceutical Technology* (New York: Marcel Dekker, 1992), volume 9). For the preparation of microemulsions, surfactant (emulsifier), co-surfactant (co-emulsifier), an oil phase and a water phase are necessary. Suitable surfactants include any surfactants that are useful in the preparation of emulsions, e.g., emulsifiers that are typically used in the preparation of creams. The co-surfactant (or "co-emulsifer") is generally selected from the group of polyglycerol derivatives, glycerol derivatives and fatty alcohols. Preferred emulsifier/co-emulsifier combinations are generally although not necessarily selected from the group consisting of: glyceryl monostearate and polyoxyethylene stearate; polyethylene glycol and ethylene glycol palmitostearate; and caprilic and capric triglycerides and oleoyl macrogolglycerides. The water phase includes not only water but also, typically, buffers, glucose, propylene glycol, polyethylene glycols, preferably lower molecular weight polyethylene glycols (e.g., PEG 300 and PEG 400), and/or glycerol, and the like, while the oil phase will generally comprise, for example, fatty acid esters, modified vegetable oils, silicone oils, mixtures of mono- di- and triglycerides, mono- and di-esters of PEG (e.g., oleoyl macrogol glycerides), etc.

Dry powder formulations for pulmonary delivery include the active agent and any carrier suitable for pulmonary drug administration may be used, although pharmaceutical sugars are generally preferred as carriers, e.g., fructose, galactose, glucose, lactitol, lactose, maltitol, maltose, mannitol, melezitose, myoinositol, palatinite, raffinose, stachyose, sucrose, trehalose, xylitol, hydrates thereof and combinations thereof. Selected components are initially combined and then blended to form a homogeneous, uniform powder mixture. Techniques for preparation of such powders are well known in the art; briefly, the preparation typically includes the steps of reducing the particle size of each component (as necessary), combining the individual components and blending. Techniques of reducing the particle size employ, by way of example, mills such as an air-jet mill or ball mill. Particle sizes having a diameter of between about 0.1 $\mu$m to about 65 $\mu$m are required for pulmonary administration. Blending methods include passing the combined powders through a sifter and blending the individual powders in a powder blender such as a "double cone" blender or a "V-blender." Regardless of technique employed the resulting powder must be both homogeneous and uniform. Typically, the active agents will make up from about 0.10% to about 99% (w/w) of the total formulation.

Pulmonary formulations of the present invention may also be administered as aerosol compositions. Aerosol formulations are known to those skilled in the art and described, for example, in *Remington: The Science and Practice of Pharmacy*, supra. Briefly, the aerosol formulation of the invention is either a solution aerosol, in which the active agents are soluble in the carrier (e.g., propellant), or a dispersion aerosol, in which the active agents are suspended or dispersed throughout the carrier or carriers and optional solvent. In aerosol formulations, the carrier is typically a propellant, usually a liquefied gas or mixture of liquified gases. For example, the carrier may be a fluorinated hydrocarbon. Preferred fluorinated hydrocarbons are selected from trichloromonofluoromethane, dichlorodifluoromethane, dichlorotetrafluoroethane, chloropentafluoroethane, 1-chloro-1,1-difluoroethane, 1,1-difluoroethane, octafluorocyclobutane, 1,1,1,2-tetrafluoroethane (HFA-134a), 1,1,1,2,3,3,3-heptafluoropropane (HFA-227) and combinations thereof. As is readily appreciated by one skilled in the art, the aerosol formulations of the invention may include one or more excipients. The aerosol formulations may, for example, contain: a solvent (e.g., water, ethanol and mixtures thereof) for increasing the solubility of the active agent; an antioxidant (e.g., ascorbic acid) for inhibiting oxidative degradation of the active agents; a dispersing agent (e.g., sorbitan trioleate, oleyl alcohol, oleic acid, lecithin, corn oil, and combinations thereof) for preventing agglomeration of particles; and/or a lubricant (e.g., isopropyl myristate) for providing slippage between particles and lubricating the components, e.g., the valve and spring, of the inhaler.

As described with respect to the dry powder formulations, the particle size released from aerosol formulations must be appropriate for pulmonary administration. Solution aerosols inherently produce small particles upon actuation of the inhaler because the active agent is expelled along with the carrier, i.e., propellant, solution as it evaporates. Consequently, solution aerosol administration produces sufficiently small particles, e.g., within a range of about 0.1 $\mu$m to about 65 $\mu$m, of active agents. Dispersion aerosols, however, contain undissolved active agents in which particle size remains constant, i.e., the size of the particles in the dispersion aerosol remains unchanged during delivery of the active agent. The active agents must therefore have an appropriate particle size before formulation into a dispersion aerosol. Thus, techniques for reducing the particle size of active agents as described above for the dry powder formulations are equally applicable for preparing active agents having an appropriate particle size in a dispersion aerosol. Further, the same ranges of particle sizes preferred for the dry powder formulations are applicable to dispersion aerosols.

Aerosol formulations of the invention may be prepared by utilizing a cold filling process. First, the components of the aerosol formulation and an aerosol container are cooled to about −40° C., so that the carrier, i.e., propellant, is a liquid. All the components except for the carrier are then placed into the aerosol container. Next, the carrier is added and the components are mixed. A valve assembly is then inserted into place. Finally, the valve assembly is crimped so that the container is airtight. The assembled container bearing the inhalant formulation may be allowed to return to ambient temperature after assembly. As an alternative to the cold filling process, the aerosol formulation may be prepared by transfer of a carrier from a bulk container after all the components except for the carrier are placed into an aerosol container and a valve assembly is then inserted and crimped into place. The liquid carrier is then metered under pressure through the valve assembly from a bulk container or tank. After the carrier is metered in, the container is checked to ensure that the pressurized contents do not leak. For both of these methods of preparing aerosol formulations, the active agent will typically make up from about 0.1 wt. % to about 40 wt. % of the total formulation. Preferably the active agents make up about 1 wt. % to about 15 wt. % of the total formulation.

The pulmonary formulations of the present invention may also be a liquid composition for inhalation, as well known in the art. See, e.g., *Remington: The Science and Practice of Pharmacy*, supra. Preferably, the liquid is an aqueous suspension, but aqueous solutions may also be used. The liquid formulations include one or more carriers in addition to the active agents. Generally the carrier is a sodium chloride solution having concentration making the formulation isotonic relative to normal body fluid. In addition to the carrier, the liquid formulations may contain water and/or excipients including an antimicrobial preservative (e.g., benzalkonium chloride, benzethonium chloride, chlorobutanol, phenylethyl alcohol, thimerosal and combinations thereof), a buffering agent (e.g., citric acid, potassium metaphosphate, potassium phosphate, sodium acetate, sodium citrate, and combinations thereof), a surfactant (e.g., polysorbate 80, sodium lauryl sulfate, sorbitan monopalmitate and combinations thereof), and/or a suspending agent (e.g., agar, bentonite, microcrystalline cellulose, sodium carboxymethylcellulose, hydroxypropyl methylcellulose, tragacanth, veegum and combinations thereof). Combining the components followed by conventional mixing effects a liquid formulation suitable for inhalation. Typically, the active agents will make up from about 0.01% to about 40% of the total formulation.

Various known devices may be used to administer pulmonary formulations, whether dry powder, aerosol or liquid. Dry powder inhalers are well known to those skilled in the art and are used to administer the aforementioned dry powder formulations. Suitable dry powder inhalation devices for administering the present formulations include, for example, TURBOHALER® (Astra Pharmaceutical Products, Inc., Westborough, Mass.), ROTAHALER® (Allen & Hanburys, Ltd., London, England). Aerosol formulations may be administered via pressurized metered-dose inhalers. Liquid formulations of the invention may be administered via a pump spray bottle or nebulizer.

Other active agents may also be included in the formulations of the invention, including other anti-inflammatory agents that dilate the airway and effect deeper delivery, especially for COPD involving inflammation of the alveoli. Agents that perform both these functions, notably long acting $\beta$ adrenergic agonists, including salmeterol xinafoate, and phosphodiesterase inhibitors, including the hypoxanthine theophylline, have been shown to exert a synergistic antiinflammatory effect in inflammatory pathophysiologic processes in the lung by Pang et al. (2000) *Am. J. Respir. Cell Mol. Biol.* 23(1):79–85.

Examples of suitable additional active agents to be coadministered with resveratrol in the treatment of inflammatory respiratory disorders include, without limitation, bronchodilators, including $\beta$ adrenergic agonists, anticholinergics, phosphodiesterase inhibitors suitable for inhalation, and corticosteroids. Combinations of bronchodilators may also be used. Long acting $\beta$ adrenergic agonists are particularly preferred, as they will not only provide antiinflammatory action but may also effect deeper delivery into the lung; this is especially important for alveolar inflammatory disease. Likewise, any glucocorticoid therapeutically suitable for administration by inhalant or a pharmaceutically suitable salt ester or other derivative thereof may be included for co-administration by inhalant.

As alluded to above, bronchodilators are useful to ensure delivery of active agent deep into the lungs. This is especially important for COPD and in ILD where inflammation is found within the alveoli. Typical bronchodilators of the anticholinergic type include, by way of example rather than limitation, atropinic compounds such as isatropium, which have been shown to be strongly synergistic (Dusser (1998) Ann. Fr. Anesth. Reanim. 17(Suppl. 2):40s–42s) with β agonists, specifically β₂ agonists, in bronchodilation for acute asthma and are expected to exert similar effects when used to open the airways to ensure deep delivery to the alveoli for delivery of antiinflammatory agent. Typical bronchodilators of the β adrenergic agonist class include, but are not limited to, albuterol, bitolterol, clenbuterol, fenoterol, formoterol, levalbuterol (i.e., homochiral (R)-albuterol), metaproterenol, pirbuterol, procaterol, reproterol, rimiterol, salmeterol and terbutaline. The bronchodilator may be present in the formulation as a salt, ester, amide, prodrug, or other derivative, or may be functionalized in various ways as will be appreciated by those skilled in the art.

Other antiinflammatory drugs can be combined with resveratrol, with the general expectation that the resulting combination will be synergistic, and may be identified from the numerous examples of synergistic antiinflammatory combinations known in the art. Corticosteroids and non-steroidal antiinflammatory drugs (NSAIDS) are potential combinatorial therapy agents, and already used in the treatment of inflammatory airway disease. Cromolyn sulfate and the new class of leukotriene inhibitors are also used in treating inflammatory disease. Agents that are not primarily antiinflammatory which have been evidenced to have antiinflammatory activity include the long acting β agonists and theophylline, as noted above, and macrolide antibiotics (Cazzola (2000) supra), which include erythromycin and its derivatives, e.g., azithromycin and clarithromycin.

The method and formulations of the invention are useful for treating humans and animals suffering from or prone to certain lung conditions, disorders or diseases associated with or caused by local inflammation. For example, the compositions find utility in the prevention or treatment of local inflammation of the lung seen in atopic and non-atopic asthma and COPD. COPD includes chronic bronchitis and emphysema. Interstitial lung disease (ILD) includes fibrosing alveolitis, sarcoidiosis and fibrotic lung diseases. The cause of ILD is unknown but may be asociated with exposure to inorganic and organic dusts or radiation, including occupational end environmental exposure. Hypersensitivity alveolitis caused by allergens can lead to ILD; idiopathic ILD is of an unknown origin and likely includes autoimmune alveolitis. Occupational inflammatory diseases of the lung that can result in ILD include asbestosis, pulmonary berylliosis, coal worker's pneumoconiosis, silicosis and byssinosis (cotton dust). The invention is additionally useful for the chemoprevention of the debilitating fibrotic involvement of ILD without the potential disadvantages associated with long-term corticosteroid therapy, when treatment is instigated before or early in the pathogenesis of fibrosis, e.g., at the stage or prior to the stage when the lung inflammation is an asymptomatic pathophysiologic process.

The invention is also useful as a substitute for corticosteroids, for example in the treatment of patients exhibiting significant systemic side effects in response to corticosteroid administration, e.g., HPA regulatory endocrine insufficiency. The invention is also useful as a substitute for glucocorticoids in the mono- or combination therapy of asthmatic patients who are resistant, a condition wherein the local inflammatory process in the lung are histologically unresponsive to steroids. The invention is further useful as a substitute to corticosteroids in combination or monotherapy in steroid naive patients to preserve the steroid naive status, for example in children where minor systemic endocrine effects can have serious developmental consequences. The invention is analogously useful in an alternating regime using either a corticosteroid or inhaled agent of the invention in combination or mono-therapy. The invention is also useful in the treatment of inflammatory respiratory conditions in immunocompromised patients, including patients immunocompromised by HIV disease.

The method and formulations of the invention can also be used as chemopreventive compositions, especially for chronic fibrotic disease such ILD and to prevent irreversible airway narrowing and lung destruction in COPD. In chemoprevention, patients deemed at risk or in the early stages of histopathologically ascertainable inflammatory disease are treated prior to development of significant pulmonary obstruction as measured by changes in forced expiratory and inspiratory volume, hypoxemia ($O_2$ level) or respiratory acidosis whether compensated or uncompensated metabolically.

The dose of active agent is in the range of about 0.015 to about 135 mg per kg per day, preferably about 0.80 to about 100 mg per kg per day for oral administration, preferably in 1 to 8 doses per day. For pulmonary administration the dose of active agent is in the range of about $1.67 \times 10^{-5}$ to about 0.66 mg per kg per day, preferably about 0.066 to about 0.66 mg per kg per day, preferably in 1 to 8 doses per day. It will be recognized by those skilled in the art that the optimal quantity and spacing of individual dosages will be determined by the nature and extent of the condition being treated, the mode of administration, and the particular individual undergoing treatment, and that such optimums can be determined by conventional techniques. That is, an optimal dosing regimen for any particular patient, i.e., the number and frequency of doses, can be ascertained using conventional course of treatment determination tests.

It is to be understood that while the invention has been described in conjunction with the preferred specific embodiments thereof, the foregoing description, as well as the examples which follow, are intended to illustrate and not limit the scope of the invention. Other aspects, advantages and modifications will be apparent to those skilled in the art to which the invention pertains.

All patents, patent documents, and publications cited herein are hereby incorporated by reference in their entireties.

EXPERIMENTAL

The following examples are put forth so as to provide those of ordinary skill in the art with a complete disclosure and description of how to make and use the formulations of the invention, and are not intended to limit the scope of what the inventors regard as their invention. Efforts have been made to ensure accuracy with respect to numbers (e.g., amounts, temperature, etc.) but some errors and deviations should be accounted for. Unless indicated otherwise, parts are parts by weight, temperature is in ° C. and pressure is at or near atmospheric. All solvents, reagents and formulation components were of Pharmaceutical Grade.

Example 1

Effect of Resveratrol to Inhibit iNOS Expression and Activity Compared to Steroids in Human Primary Epithelial Cells:

The inducible form of the enzyme NO synthase, iNOS (NOS2), which is known to be expressed during inflammation, is thought to be responsible for increased NO levels of asthmatic patients. Agents known to induce iNOS in human primary epithelial cells, such as interleukin-1β, tumor necrosis factor-α, and interferon-γ (cytomix) are useful in assaying resveratrol for inhibition of iNOS expression and activity, and comparing its effect to steroids.

Human primary epithelial cells are cultured from normal donor tissue. Explant cultures of tissue obtained from normal human lung transplant donors provided human primary epithelial (HPE) cells. The HPE cells were cultured in Ham's F12 nutrient medium containing 5% (v/v) fetal calf serum (FCS), 1 μM hydrocortisone, 5 ng/ml EGF (epithelial growth factor), 10 μg/ml insulin, 10 nM retinoic acid, 0.5 μg/ml transferrin, 2 μg/ml triiodothyronine, 1.5 μg/ml NaHCO$_3$, 100 μg/ml penicillin, 100 μg/ml streptomycin and 0.25 μg/m amphotericin B; the cells were incubated at 37° C. in a humidified atmosphere containing 95% (v/v) air, 5% (v/v) CO$_2$. The HPE cells were cultured for the last 24 hours prior to the experimental treatments under the same conditions except that additive free Ham's F12 media was substituted for the supplemented Ham's F12 media described above.

These cells were stimulated for 24 hours with 50 ng/ml cytomix (interferon-γ) in the absence or presence of resveratrol, or one of glucocorticoids, dexamethasone and budenoside. Activity of iNOS is measured by determination of nitrate and nitrite/nitrate accumulation. Nitrite was measured by a modification of the method of Misko, et al. (1993) *Anal. Biochem.* 214:11–16. Briefly the supernatant cleared from centrifugation at 10,000 g for 10 minutes, of a mixture of 200 μl of media or standard solution and 100 μl of 2% (w/v) charcoal in 0.2% (w/v) dextran, was mixed with 10 μl of 0.05 mg/ml 2,3-diaminonaphthalene in 0.625M HCl and incubated in the dark for 10 minutes. The reaction was stopped by addition of 10 μl of 1.4M NaOH, and fluorescense was measured with a Biolite F1 fluorimeter (Labtech, Uckfield, U.K.) set at: 460 nm emission wavelength, 360 nm excitation wavelength, 40–50% sensitivity. Sample nitrite concentration was calculated by reference to a standard curve of known nitrite concentrations, permitting assay sensitivity to 0.1 μM.

Resveratrol was the only agent able to inhibit nitrite formation. Both dexamethasone and budesonide failed to inhibit nitrite accumulation in the cell culture media at concentrations in the range of $10^{-9}$ M to $10^{-5}$ M. EC$_{50}$ values were determined to be 3.6±2.9 μM for nitrite accumulation and 0.88±0.47 μM for nitrite/nitrate accumulation. Expression of mRNA for iNOS was evaluated by RT-PCR of RNA extracted from the cells using the Qiagen RNeasy mini kit as directed by the manufacturer (Crawley, Sussex, U.K.). RT-PCR was performed according to routine methods. Briefly, reverse transcription was performed on 5 μg of RNA heated to 70° C. for 5 minutes prior to being incubated for one hour at 42° C. in a solution for reverse transcription (in 1× reverse transcriptase buffer: AMV reverse transcriptase: 0.25 μg/μl; deoxynucleotide triphosphates (dNTP): 1.0 mM; RNAsin: 1 μg/μl; and random primers: 0.01 μg/μl) followed by denaturation at 90° C. for 4 minutes, and dilution by addition of 80 μl of H$_2$O. PCR was performed on the resultant cDNA using 5 μl of the preceding solution incubated in a final volume of 25 μl containing, in addition to the cDNA: 1×KCl buffer, 2 mM dNTP, 5 ng/μl specific primers, and 0.02 μg/μl Taq polymerase (forward primer: 5'-GAGCTTCTACCTCAAGCTATC-3' (SEQ. ID. No. 1); reverse primer: 5'-CCTGATGTTGCCATTGTTGGT-3' (SEQ. ID. No. 2); T cycles used: [94° C. for 45 seconds\56° C. for 45 s\72° C. for 60 s]-32 cycles followed by 10 minutes at 72° C.). RT-PCR of GAPDH was performed as an internal control (forward primer: 5'-ATTCCATGGCACCGTCAAGGCT-3' (SEQ. ID. No. 3); reverse primer: 5'-TCAGGTCCACCACTGACACGT-3' (SEQ. ID. No. 4); T cycles used: [94° C. for 45 seconds\56° C. for 45 s\72° C. for 60 s]-26 cycles followed by 10 minutes at 72° C.). Specific primers for iNOS PCR gave a PCR product of 312 bp; specific primers for GADPH PCR gave a PCR product of 571 bp. PCR products were identified on 2% (w/v) agarose gel. Samples that did not contain reverse transcriptase were employed as negative controls.

Primary epithelial cells were treated for 4 hours with cytomix in the presence of resveratrol, or one of dexamethasone and budenoside, and assayed for iNOS mRNA. Only resveratrol inhibited iNOS expression as measured by mRNA.

Example 2

Inhibition of Inflammatory Gene Expression and IL-8 Release by Resveratrol Compared to Steroids in Human Airway Epithelial Cells:

The human airway epithelial cell line A549 may be employed to study resveratrol inhibition of the release of IL-8 (interleukin 8) and GM-CSF (granulocyte macrophage-colony stimulating factor) by a 1 ng/ml stimulation with IL-1β (interleukin 1β). A549 cells, BEAS-2B cells and 16HBE-16o⁻ cells were stimulated with 1 ng/ml levels of IL-1β in the presence of resveratrol.

Cells, including the A549 cells, were cultured in Dulbecco's modified Eagle's medium (DMEM) 10% (v/v) fetal calf serum (FCS), 100 μg/ml penicillin and 100 μg/ml streptomycin. IL-8 release was measured by commercially available ELISA kit (R&D Systems). The EC$_{50}$ for inhibition of the release of IL-8 by these cells was determined to be 111±2.9 μM for the BEAS-2B cells, 8.9±3.5 μM for the 16HBE-16o⁻ cells and 72±11 μM for the A549 cells. Resveratrol also inhibited GM-CSF release in A549 cells stimulated with 1 ng/ml IL-1β with an EC$_{50}$ of 22±8 μM.

GM-CSF release was measured in culture media by sandwich assay employing rat monoclonal capture antibody (Ab, mAb) against GM-CSF and a biotinylated rat anti-human GM-CSF mAb. The rat capture mAb against GM-CSF, diluted 1:500 in 0.1 M NaHCO$_3$, was coated overnight at 4° C. onto 96 well plates. After washing, with wash buffer (NaCl: 145 mM, KCl: 4 mM, NaH$_2$PO$_4$: 10 mM, Tween-20: 0.05% (v/v), pH: 7.4) the plates were blocked by application of 10% (v/v) FCS at room temperature for 2 hours. After washing, samples and standards were added to the well plates and incubated at 4° C. overnight. After additional extensive washing, the plates were incubated for 45 minutes with biotinylated rat anti-human GM-CSF mAb diluted 1:1000 in 10% (v/v) FCS in wash buffer, and then incubated for 30 minutes with a 1:400 dilution of avidin-peroxidase in 10% (v/v) FCS in wash buffer.

The plates were then developed with ABTS substrate solution (2,2' azino-bis(3-ethylbenzthiazoline-6-sulphonic acid): 0.547 mM, citric acid: 0.1 M pH: 4.35, H$_2$O$_2$: 0.03% (v/v)) The developed plates were measured for absorbance at 405 nm and GM-CSF calculated by reference to a standard curve, permitting a 32 pg GM-CSF/ml detection limit.

The expression of inflammatory genes was then evaluated in cells transformed with luciferase reporter genes containing sites for transcription factors (Tf, Tfs). The A549 cells were stably transfected by routine methods with luciferase reporters containing the transcription factors NF-κB, TRE (AP-1, TPA responsive element) and CRE (cAMP responsive element). Luciferase activity of cell lysates resuspended in 100 mml cell lysis buffer mixed (40 mml resuspended lysate: 40 mml assay reagent) was measured using the Luciferase Assay System (Promega), with emitted light measured by a Turner DesignsTD-20/20 luminometer (Steptech Instruments Ltd., Stevenage, U.K.)

Resveratrol inhibited NF-κB dependent transcription completely with an $EC_{50}$ value of $21\pm7$ μM. Dexamethasone inhibited NF-KB dependent transcription by only 41% with an $EC_{50}$ value of $16\pm12$ μM. Resveratrol inhibited TRE dependent transcription by 85% with an $EC_{50}$ value of $7\pm4$ μM. Dexamethasone inhibited CRE dependent transcription by 62% with an $EC_{50}$ value of $3.4\pm3$ μM. Resveratrol inhibited CRE dependent transcription by 91% with an $EC_{50}$ value of $30\pm17$ μM. Dexamethasone inhibited CRE dependent transcription by 62% with an $EC_{50}$ value of $3.4\pm3$ μM.

Example 3

Oral Administration of Resveratrol for Treating Asthma:

Resveratrol is evaluated clinically for efficacy in treating asthma. The methods of the following references are generally used in the evaluation of asthmatic disease: Wohl et al. (2000) N. Engl. J. Med. 343(15):1113–4; Agertoft et al. (2000) N. Engl. J. Med. 343(15):1064–9. Patients with asthma are treated once or more per day with gelatin capsules containing resveratrol. Patients are divided randomly and blindly into four approximately equal groups that receive either 0 (placebo), 200, 2000, or 3000 mg/day resveratrol for about six months in oral doses of 0, 50, 500, or 750 mg administered 4 times daily for about six months. Patients are medically monitored for clinical symptoms of asthma throughout the study, including frequency and severity of acute asthma attacks. In addition, blood serum and induced sputum samples are obtained from the patients at days 0, 30, 90, and 180 and are assayed for IL-8 (Tang et al. (2000) J. Asthma 37(5):409–13 [describing use of serum IL-8 (sIL-8)]) and eosinophil cationic protein (ECP) (Baba et al. (2000) J. Asthma 37(5):339–408 [describing use of serum ECP (sECP)]) by routine methods. In addition exhaled nitric oxide (NO) and carbon monoxide (CO) levels may be measured at more frequent intervals, such as every other week. Forced expiratory volume (FEV) and forced inspiratory volume (FIV) are also evaluated to measure airway patency as a direct measure of clinical morbidity and to determine correlation the histopathologic and other indicators of clinical disease, such as exhaled NO Immunhistopathologic examination of lung tissue biopsy samples taken at the same intervals as the blood samples are also examined for histopathologic evidence of extent and histology of inflammation. Experimental work conducted according to the documented procedures shows that resveratrol and related compounds of this invention are effective for treating asthma.

Example 4

Pulmonary Administration of Resveratrol for Treating Asthma:

Resveratrol is evaluated clinically for efficacy in treating asthma when administered pulmonarily. The methods of the following references are generally used in the evaluation of asthmatic disease: Wohl et al. (2000) N. Engl. J. Med. 343(15):1113–4; Agertoft et al. (2000) N. Engl. J. Med 343(15):1064–9. Patients with asthma are treated once or more per day with inhalator delivered pulmonary administered doses of resveratrol. Patients are divided randomly and blindly into approximately equal groups that receive either 0 (placebo), 4, 8, or 20 mg/day resveratrol in inhaled doses of 0, 1, 2, or 5 mg administered 4 times daily for about six months. Patients are medically monitored for clinical symptoms of asthma throughout the study, including frequency and severity of acute asthma attacks. In addition, blood serum and induced sputum samples are obtained from the patients at days 0, 30, 90, and 180 and are assayed for IL-8 (Tang et al. (2000) J. Asthma 37(5):409–13 [describing use of serum IL-8 (sIL-8)]) and eosinophil cationic protein (ECP) (Baba et al. (2000) J. Asthma 37(5):339–408 [describing use of serum ECP (sECP)]) by routine methods. In addition exhaled nitric oxide (NO) and carbon monoxide (CO) levels may be measured at more frequent intervals, such as every other week. Forced expiratory volume (FEV) and forced inspiratory volume (FIV) are also evaluated to measure airway patency as a direct measure of clinical morbidity and to determine correlation the histopathologic and other indicators of clinical disease, such as exhaled NO Immunhistopathologic examination of lung tissue biopsy samples taken at the same intervals as the blood samples are also examined for histopathologic evidence of extent and histology of inflammation. Experimental work conducted according to the documented procedures shows that resveratrol and related compounds of this invention are effective for treating asthma.

Example 5

Comparison of Oral or Inhaled Resveratrol and Inhaled Glucocorticoids for Treating COPD in Steroid Naive Patients:

Steroid naive patients suffering from different COPDs patients are selected and divided into populations according to the COPD. Chronic bronchitis populations and emphysema populations are appropriately studied. The populations are divided in terms of progression of their COPD into subpopulations early or mild, mid-stage or moderate, and advanced impairment of lung function. The study is generally patterned after the asthma studies with modifications appropriate to the clinical and histopathologic evaluation of COPD disease, and the references listed in the preceding examples may be applied as appropriate. One major difference is that the COPD study should last for 1 to 2 years or longer, because of the chronic nature of COPD. Each subpopulation is divided equally and randomly into three groups. The first group is treated with oral resveratrol, with the group subdivided randomly and blindly into four approximately equal subgroups that receive either 0 (placebo), 200, 2000, or 3000 mg/day resveratrol for about 12 to 24 months in oral doses of 0, 50, 500, or 750 mg administered 4 times daily for about 12 to 24 months. The second group is treated with pulmonary resveratrol, with the group subdivided randomly and blindly into four approximately equal subgroups that receive either 0 (placebo), 4, 8, or 20 mg/day resveratrol in inhaled doses of 0, 1, 2, or 5 mg administered 4 times daily for about 12 to 24 months. The third group is treated with pulmonary budenoside, with the group subdivided randomly and blindly into four approximately equal subgroups that receive either 0 (placebo), 200, 400, or 800 μg/day budenoside in once daily inhaled doses (the doses can be divided for 4x daily administration, but this is not neccessary due to the relatively long plasma and tissue half-life of steroids).

Patients are medically monitored for clinical symptoms of COPD throughout the study, including frequency and severity of hypoxemic and respiratiry acidotic exacerbations. In addition, blood serum and induced sputum samples are obtained from the patients at days 0, 30, 60, 90, 120, 180 and every 30 days thereafter, and neutrophil counts are performed and the samples are assayed for IL-8 and myeloperoxidase activity by routine methods. In addition exhaled nitric oxide (NO) and carbon monoxide (CO) levels may be measured at more frequent intervals, such as every other week. Forced expiratory volume (FEV) and forced inspiratory volume (FIV) are also evaluated to measure airway patency as a direct measure of clinical morbidity and to determine correlation the histopathologic and other indicators of clinical disease. Immunhistopathologic examination of lung tissue biopsy samples taken at the same intervals as the blood samples are also examined for histopathologic evidence of extent and histology of inflammation. Experimental work conducted according to the documented procedures shows that pulmonary delivered and oral resveratrol and related compounds of this invention are more effective for treating COPD than inhaled steroids, and exhibit fewer systemic effects than patients treated with inhaled glucocorticosteroids. COPD is shown to be more responsive to the therapy in earlier compared to more progressive disease.

Example 6
Resveratrol Substitution for Glucocorticoids vs. Initiation of Steroids in Treatment of Asthma:

Asthmatic steroid naive children with asthma disease severe enough to require chronic pulmonary steroid therapy are divided randomly and blindly into three groups. The duration of the study should be long, as pulmonary steroids for asthma are a chronic therapy, thus 1 to 2 years or more is optimal. The first group is treated with oral resveratrol, with the group subdivided randomly and blindly into four approximately equal subgroups that receive either 0 (placebo), 200, 2000, or 3000 mg/day resveratrol for about 12 to 24 months in oral doses of 0, 50, 500, or 750 mg administered 4 times daily for about 12 to 24 months. The second group is treated with pulmonary resveratrol, with the group subdivided randomly and blindly into four approximately equal subgroups that receive either 0 (placebo), 4, 8, or 20 mg/day resveratrol in inhaled doses of 0, 1, 2, or 5 mg administered 4 times daily for about 12 to 24 months. The third group is treated with pulmonary budenoside, with the group subdivided randomly and blindly into four approximately equal subgroups that receive either 0 (placebo), 200, 400, or 800 µg/day budenoside in once daily inhaled doses (the doses can be divided for 4× daily administration, but this is not neccessary due to the relatively long plasma and tissue half-life of steroids).

The methods of the following references may be used in the evaluation of asthmatic disease: Wohl et al. (2000) *N. Engl. J. Med.* 343(15):1113–4; Agertoft et al. (2000) *N. Engl. J. Med.* 343(15):1064–9. Patients are medically monitored for clinical symptoms of asthma throughout the study, including frequency and severity of acute asthma attacks. In addition, blood serum and induced sputum samples are obtained from the patients at days 0, 30, 90, and 180 and are assayed for IL-8 (Tang et al. (2000) *J. Asthma* 37(5):409–13 [describing use of serum IL-8 (sIL-8)]) and eosinophil cationic protein (ECP) (Baba et al. (2000) *J. Asthma* 37(5):339–408 [describing use of serum ECP (sECP)]) by routine methods. In addition exhaled nitric oxide (NO) and carbon monoxide (CO) levels may be measured at more frequent intervals, such as every other week. Forced expiratory volume (FEV) and forced inspiratory volume (FIV) are also evaluated to measure airway patency as a direct measure of clinical morbidity and to determine correlation the histopathologic and other indicators of clinical disease, such as exhaled NO. Immunhistopathologic examination of lung tissue biopsy samples taken at the same intervals as the blood samples are also examined for histopathologic evidence of extent and histology of inflammation. Experimental work conducted according to the documented procedures shows that oral and pulmonary resveratrol and related compounds of this invention are effective as substitutes for antiinflammatory treatment with inhaled steroids in treating asthma, and may be clinically substituted for inhaled glucocorticoids with equal therapeutic effect on all measured parameters and reduced systemic side effects including reduced suppression of growth upon instigation of therapy.

Example 7
Evaluation of Resveratrol Supplementation for Glucocorticoids vs. Increasing Dose of Steroids in Treatment of Steroid Resistant Asthma:

Instead of steroid naive chid asthmatic patients (children are chosen because of the increased gravity of systemic endocrine effects for children, but adults can be analogously studied) selected in Example 6, patients reesistant to existing pulmonary steroid therapy are selected. The study is otherwise analogous to the study in Example 7, except that in the first two groups the oral or inhaled resveratrol supplements the inhaled steroid dose being administered prior to the beginning of the evaluation, while the third group has the dosage of inhaled steroid being administered prior to the study doubled. Alternatively the third group can receive oral prednisone in the appropriate systemic dose. The evaluation is otherwise performed identically to that in Example 6. Experimental work conducted according to the documented procedures shows that oral and pulmonary resveratrol and related compounds of this invention are as or more effective as supplements to existing steroid therapy for antiinflammatory treatment than doubling inhaled steroid dose in treating asthma. Resveratrol supplementation is therefore clinically preferable to increasing inhaled glucocorticoids with equal or better therapeutic effect on all measured parameters and reduced systemic side effects compared with doubling steroid dosage, including reduced suppression of growth upon instigation of increased dose.

Example 8
Clinical Evaluation of Oral Resveratrol for Treating COPD:

Resveratrol is evaluated clinically for efficacy in treating COPD. The study is generally patterned after the asthma studies with modifications appropriate to the clinical and histopathologic evaluation of COPD disease, and the references listed in the preceding examples may be applied as appropriate. Smokers are treated once or more per day with gelatin capsules containing resveratrol. The different populations of COPD patients are subdivided into subpopulations: emphysema patients, bronchitis patients and other COPD. Patients are divided randomly and blindly into four approximately equal groups that receive either 0 (placebo), 200, 2000, or 3000 mg/day resveratrol for about six months in oral doses of 0, 50, 500, or 750 mg administered 4 times daily for about six months.

Patients are medically monitored for clinical symptoms of COPD throughout the study, including frequency and severity of hypoxemic and respiratiry acidotic exacerbations. In addition, induced sputum samples are obtained from the patients at days 0, 30, 90, and 180 and neutrophil counts are performed and the samples are assayed for IL-8 and myeloperoxidase by routine methods. Forced expiratory volume (FEV) and forced inspiratory volume (FIV) are also evaluated to measure airway patency as a direct measure of clinical morbidity and to determine correlation the histopathologic and other indicators of clinical disease. Immunhistopathologic examination of lung tissue biopsy samples taken at the same intervals as the blood samples are also examined for histopathologic evidence of extent and histology of inflammation. Experimental work conducted according to the documented procedures shows that oral resveratrol and related compounds of this invention are effective for treating COPD.

Example 9
Clinical Evaluation of Pulmonary Resveratrol for Chemoprevention of COPD:

Pulmonary administration of resveratrol for COPD may be evaluated by the method preceding in Example 8, using the inhaled doses specified in Example 4. Specifically the subgroups receive either 0 (placebo), 4, 8, or 20 mg/day resveratrol in inhaled doses of 0, 1, 2, or 5 mg administered 4 times daily for th duration of the study. Experimental work conducted according to the documented procedures shows that pulmonary resveratrol and related compounds of this invention are effective for treating COPD.

Example 10
Evaluation of Oral Administration of Resveratrol for Chemoprevention of COPD in Smokers:

Resveratrol is evaluated clinically for efficacy in chemoprevention of COPD in smokers. The study is generally patterned after the asthma studies with modifications appropriate to the clinical and histopathologic evaluation of COPD disease, and the references listed in the preceding examples may be applied as appropriate. Smokers with no disease or mild COPD are treated once or more per day with gelatin capsules containing resveratrol. The population of smokers are subdivided into subpopulations: clinically and histopathologically disease free, clinically asymptomatic with histopathologic inflammation and mildly COPD symptomatic, meaning some chronic bronchitis but no pulmonary impairment causing hypoxemia or acidosis. Each subpopulation is divided randomly and blindly into four approximately equal groups that receive either 0 (placebo), 200, 2000, or 3000 mg/day resveratrol for about six months in oral doses of 0, 50, 500, or 750 mg administered 4 times daily for 2 to 5 years. The study should be conducted as long as the patient population can be followed.

Patients are medically monitored for clinical symptoms of COPD throughout the study, including onset of symptoms and frequency and severity thereof. In addition, induced sputum samples are obtained from the patients at days 0, 30, 60, 90, 120, 180 and every 30 days thereafter, and neutrophil counts are performed and the samples are assayed for IL-8 and myeloperoxidase by routine methods. Forced expiratory volume (FEV) and forced inspiratory volume (FIV) are also evaluated to measure airway patency as a direct measure of clinical morbidity and to determine correlation the histopathologic and other indicators of clinical disease. Immunhistopathologic examination of lung tissue biopsy samples taken at the same intervals as the blood samples are also examined for histopathologic evidence of extent and histology of inflammation. Experimental work conducted according to the documented procedures shows that oral resveratrol and related compounds of this invention are effective for chemoprevention of COPD in smokers without significant side effects that would be expected from steroid administration, with the chemoprevention most effective when instituted as early as possible in the pathophysiologic process. This study can be analogously performed for pulmonary administration of resveratrol in the doses stated in the preceding examples.

Example 11
Evaluation of Oral Administration of Resveratrol for Chemoprevention of ILD in Individuals at Risk:

Resveratrol is evaluated clinically for efficacy in chemoprevention of ILD in smokers. The study is generally patterned after the COPD chemoprevention study (Example 10) with modifications appropriate to the clinical and histopathologic evaluation of ILD, and the references listed in the preceding examples may be applied as appropriate. Individuals at risk with no disease or mild COPD are treated once or more per day with gelatin capsules containing resveratrol. A population of individuals at risk for a specific ILD, such as silicosis can be studied, or several such populations such as sand blasters (silicosis) and coal miners can be studied in parallel The different populations are subdivided into subpopulations: clinically and histopathologically disease free, clinically asymptomatic with histopathologic inflammation and mildly ILD symptomatic, meaning some fibrosis but no pulmonary impairment causing hypoxemia or acidosis. Each subpopulation is divided randomly and blindly into four approximately equal groups that receive either 0 (placebo), 200, 2000, or 3000 mg/day resveratrol for about six months in oral doses of 0, 50, 500, or 750 mg administered 4 times daily for 2 to 5 years. The study should be conducted as long as the patient population can be followed.

Patients are medically monitored for clinical symptoms of ILD throughout the study, including onset of symptoms and frequency and severity thereof. In addition, induced sputum samples are obtained from the patients at days 0, 30, 60, 90, 120, 180 and every 30 days thereafter, and neutrophil counts are performed and the samples are assayed for IL-8 and myeloperoxidase by routine methods. Forced expiratory volume (FEV) and forced inspiratory volume (FIV) are also evaluated to measure airway patency as a direct measure of clinical morbidity and to determine correlation the histopathologic and other indicators of clinical disease. Immunhistopathologic examination of lung tissue biopsy samples taken at the same intervals as the blood samples are also examined for histopathologic evidence of extent and histology of inflammation. Experimental work conducted according to the documented procedures shows that oral resveratrol and related compounds of this invention are effective for chemoprevention of ILD without significant side effects that would be expected from steroid administration, with the greatest chemopreventive effect found when the therapy is instituted as early in the histopathologic course of the disease. This study can be analogously performed for pulmonary administration of resveratrol in the doses stated in the preceding examples.

We claim:

1. A method for treating interstitial lung disease in a patient suffering from or predisposed to developing interstitial lung disease (ILD), comprising administering to the patient a pharmaceutical formulation that comprises a pharmaceutically acceptable carrier and a therapeutically effective amount of an active agent selected from the group consisting of resveratrol, pharmacologically acceptable salts, esters, amides, prodrugs or analogs thereof, and combinations thereof.

2. The method of claim 1, wherein the active agent is cis-resveratrol or a pharmacologically acceptable salt, ester, amide, prodrug or analog thereof.

3. The method of claim 2, wherein the active agent is cis-resveratrol.

4. The method of claim 2, wherein the active agent is a conjugate of cis-resveratrol and a mono- or di-saccharide.

5. The method of claim 4, wherein the active agent is cis-resveratrol glucoside.

6. The method of claim 1, wherein the active agent is trans-resveratrol or a pharmacologically acceptable salt, ester, amide, prodrug or analog thereof.

7. The method of claim 6, wherein the active agent is trans-resveratrol.

8. The method of claim 6, wherein the active agent is a conjugate of trans-resveratrol and a mono- or di-saccharide.

9. The method of claim 8, wherein the active agent is trans-resveratrol glucoside.

10. The method of claim 1, wherein the active agent comprises a mixture of cis-resveratrol and trans-resveratrol.

11. The method of claim 1, wherein the active agent is delivered orally.

12. The method of claim 1, wherein the active agent is delivered by pulmonary administration.

13. The method of claim 1, wherein the active agent is delivered parenterally.

14. The method of claim 13, wherein the active agent is delivered to the alveoli.

15. The method of claim 1, further comprising the co-administration of an additional active agent.

16. The method of claim 15, wherein the formulation further includes an additional active agent.

17. The method of claim 16, wherein the additional active agent is selected from the group consisting of glucocorticoids, non-steroidal antiinflammatory drugs, macrolide antibiotics, bronchodilators, leukotriene receptor inhibitors, cromolyn sulfate and combinations thereof.

18. The method of claim 17, wherein the additional active agent is selected from the group consisting of phosphodiesterase inhibitors, long acting $\beta_2$ adrenergic agonists, and combinations thereof.

19. The method of claim 18, wherein the additional active agent is selected from the group consisting of theophylline, salmetrol xinafoate, and a combination thereof.

20. The method of claim 1, wherein the ILD is fibrosing alveolitis, sarcoidiosis, or fibrotic lung disease.

* * * * *